US008080637B1

(12) United States Patent
Kotwal et al.

(10) Patent No.: US 8,080,637 B1
(45) Date of Patent: Dec. 20, 2011

(54) THERAPEUTIC METHOD OF TREATING BRAIN TRAUMA IN RODENTS WITH VCP

(75) Inventors: Girish J. Kotwal, Louisville, KY (US); Ramona Hicks, Seattle, WA (US)

(73) Assignee: Kotwal Bioconsulting, LLC, Louisville, KY (US)

( * ) Notice: Subject to any disclaimer, the term of this patent is extended or adjusted under 35 U.S.C. 154(b) by 411 days.

(21) Appl. No.: 10/199,979

(22) Filed: Jul. 19, 2002

Related U.S. Application Data

(60) Provisional application No. 60/306,671, filed on Jul. 20, 2001.

(51) Int. Cl.
*C12P 21/08* (2006.01)
*C12P 21/04* (2006.01)
*A61K 38/43* (2006.01)

(52) U.S. Cl. .................... 530/387.3; 424/94.1; 435/69.7

(58) Field of Classification Search ................ 536/23.1, 536/24.5; 514/44, 2; 424/93.1, 94.1; 530/300; 800/21; 242/93.1
See application file for complete search history.

(56) References Cited

U.S. PATENT DOCUMENTS 6,140,472 A * 10/2000 Rosengard et al. ........ 530/387.3
6,184,248 B1 * 2/2001 Lee et al. ..................... 514/474

FOREIGN PATENT DOCUMENTS

WO          WO 9944625 A1 *  9/1999

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Eck, et al. (1996) Goodman & Gilman's The Pharmacological Basis of Therapeutics, 9th Ed., McGraw-Hill, New York, NY., pp. 77-101.*
Verma, et al. (1997) Nature, 389: 239-42.*
Kotwal, et al. (2002) Ann. NY. Acad. Sci., 973: 317-322.*
Statler, et al. (2001) J. Neurotrauma, 18(11): 1195-206.*
Langer (2003) Sci. Am., 288(4): 51-57.*
Rudinger (1976) Peptide Hormones, Univ. Park Press, Baltimore, MD, pp. 1-7.*
Bowie, et al. (1990) Science, 247: 1306-10.*
Stelmasiak, et al. (2000) Med. Sci. Monit., 6(2): 426-32.*
The Merck Manual, 17th Edition, Merck Research Laboratories, (1999), pp. 1022-1023.
Al-Mohanna, Futwan, et al., "Vaccinia Virus Complement Control Protein is Capable of Protecting Xenoendothelial Cells From Antibody Binding and Killing by Human Complement and Cytotoxic Cells", *Transplantation*, vol. 71, No. 6, (Mar. 27, 2001), pp. 796-801.
Bellander, Bo-Michael, et al., "Activation of the complement cascade and increase of clusterin in the brain following a cortical contusion in the adult rat", *J. Neurosurg*, vol. 85, (Sep. 1996), pp. 468-475.
Daly, J., et al., "Pro-Inflammatory Complement Activation by the Aβ Peptide of Alzheimer's Disease is Biologically Significant and Can Be Blocked by Vaccinia Virus Complement Control Protein", *Neurobiology of Aging*, vol. 19, No. 6, (1998), pp. 619-627.

Frank, M.M., et al., "The role of complement in inflammation and phagocytosis", *Immunology Today*, vol. 12, No. 9, (1991), pp. 322-326.
Furlong, S.T., et al., "C3 activation is inhibited by arralogs of compstatin but not by serine protease inhibitors or peptidyl α-ketoheterocycles", *Immunopharmacology*, vol. 48, (2000), pp. 199-212.
Hicks, R., et al., "Temporal and spatial characterization of neuronal injury following lateral fluid-percussion brain injury in the rat", *Acta Neuropathol*, vol. 91, (1996), pp. 236-246.
Horstick, G., et al., "Application of C1-Esterase Inhibitor During Reperfusion of Ischemic Myocardium Dose-Related Beneficial Versus Detrimental Effects", *Circulation*, (Dec. 2001), pp. 3125-3131.
Inal, J., et al., "Complement C2 Receptor Inhibitor Trispanning and the β-Chain of C4 Share a Binding Site for Complement C2", *The Journal of Immunology*, (2002), pp. 5213-5221.
Isaacs, S.N., et al., "Vaccinia virus complement-control protein prevents antibody-dependent complement-enhanced neutralization of infectivity and contributes to virulence", *Proc. Natl. Acad. Sci. USA*, vol. 89, (Jan. 1992), pp. 628-632.
Kaczorowski, S.L., et al., "Effect of Soluble Complement Receptor-1 on Neutrophil Accumulation After Traumatic Brain Injury in Rats", *Journal of Cerebral Blood Flow and Metabolism*, vol. 15, No. 5, (1995), pp. 860-864.
Keeling, K.L., et al., "Local neutrophil influx following lateral fluid-percussion brain injury in rats is associated with accumulation of complement activation fragments of the third component (C3) of the complement system", *Journal of Neuroimmunology*, vol. 105, (2000), pp. 20-30.
Kirschfink, M., "Controlling the complement system in inflammation", *Immunopharmacology*, vol. 38, (1997), pp. 51-62.
Kirschfink, M., "Targeting complement in therapy", *Immunological Reviews*, vol. 180, (2001), pp. 177-189.
Kotwal, G.J., "Inhibition of the Complement Cascade by the Major Secretory Protein of Vaccinia Virus", *Science*, vol. 250, (Nov. 9, 1990), pp. 827-830.
Kotwal, G.J., "Microorganisms and their interation with the immune system", *Journal of Leukocyte Biology*, vol. 62, (Oct. 1997), pp. 415-429.
Kotwal, G.J., et al., "Poxviral mimicry of complement and chemokine system components: what's the end game?", *Immunology Today*, vol. 21, No. 5, (May 2000), pp. 242-248.
Kotwal, G.J., et al., "The inflammation modulatory protein (IMP) of cowpox virus drastically diminishes the tissue damage by down-regulating cellular infiltration resulting from complement activation", *Molecular and Cellular Biochemistry* vol. 185, (1998), pp. 39-46.
Kotwal, G.J., et al., "Vaccinia virus encodes a secretory polypeptide structurally related to complement control proteins", *Nature*, vol. 335, (Sep. 8, 1988), pp. 176-178.
Levin, H.S., et al., "Neurobehavioral outcome following minor head injury: a three-center study", *J. Neurosurg.*, vol. 66, (Feb. 1987), pp. 234-243.

(Continued)

*Primary Examiner* — Robert M Kelly
(74) *Attorney, Agent, or Firm* — Angela Parsons; Fish & Richardson P.C

(57) ABSTRACT

The invention provides a method to treat a complication of neuronal injury in a mammal by inhibiting the complement cascade.

2 Claims, 3 Drawing Sheets

OTHER PUBLICATIONS

McKenzie, R., et al., "Regulation of Complement Activity by Vaccinia Virus Complement-Control Protein", *The Journal of Infectious Diseases*, vol. 166, (1992), pp. 1245-1250.

Monsinjon, T., et al., "Complement and its implications in cardiac ischemia/reperfusion: strategies to inhibit complement", *Fundamental & Clinical Pharmacology*, vol. 15, (2001), pp. 293-306.

Morgan, B.P., et al., "Expression of complement in the brain: role in health and disease", *Immunology Today*, vol. 17, No. 10, (Oct. 1996), pp. 461-466.

Murthy, Krishna H.M., et al., "Crystal Structure of a Complement Control Protein that Regulates Both Pathways of Complement Activation and Binds Heparan Sulfate Proteoglycans", *Cell*, vol. 104, (Jan. 26, 2001), pp. 301-311.

Nagahama, M., et al., "Adenovirus-mediated gene transfer of triple human complement regulating proteins (DAF, MCP and CD59) in the xenogeneic porcine-to-human transplantation model", *Transpl. Int.*, vol. 15, (2002), pp. 205-211.

Reynolds, D.N, et al., "Heparin Binding Activity of Vaccinia Virus Protein Confers Additional Properties of Uptake by Mast Cells and Attachment to Endothelial Cells", *Advances in Animal Virology*, (Nov. 1998), pp. 337-342.

Roos, A. et al., "Specific Inhibition of the Classical Complement Pathway by C1q-Binding Peptides", *The Journal of Immunology*, (2001), pp. 7052-7059.

Rosengard, A.M., et al., "Variola virus immune evasion design: Expression of a highly efficient inhibitor of human complement", *PNAS*, vol. 99, No. 13, (Jun. 25, 2002), pp. 8808-8813.

Smith, S.A., et al., "Conserved Surface-Exposed K/R-X-K/R Motifs and Net Positive Charge on Poxvirus Complement Control Proteins Serve as Putative Heparin Binding Sites and Contribute to Inhibition of Molecular Interactions with Human Endothelial Cells: a Novel Mechanism for Evasion of Host Defense" , *Journal of Virology*, (Jun. 2000), pp. 5659-5666.

Soares, H.D., et al., "Inflammatory Leukocytic Recruitment and Diffuse neuronal Degeneration Are Separate Pathological Processes Resulting from Traumatic Brain Injury", *The Journal of Neuroscience*, vol. 15, No. 12, (Dec. 1995), pp. 8223-8233.

Stahel, P.F., et al., "The role of the complement system in traumatic brain injury", *Brain Research Reviews*, vol. 27, (1198), pp. 243-256.

Strachan, A.J., et al., "Inhibition of immune-complex mediated dermal inflammation in rats following either oral or topical administration of small molecule C5a receptor antagonist", *British Journal of Pharmacology*, vol. 134, (2001), pp. 1778-1786.

Tanno, H., et al., "Breakdown of the Blood-Brain Barrier after Fluid Percussive Brain Injury in the Rat. Part 1: Distribution and Time Course of Protein Extravasation", *Journal of Neurotrauma*, vol. 9, No. 1, (1992), pp. 21-32.

Smith et al., 1991, "Evaluation of Memory Dysfunction Following Experimental Brain Injury Using the Morris Water Maze", *J. Neurotrauma*, 8:259-269.

Gennarelli, 1994, "Animate Models of Human Head Injury", *J. Neurotrauma*, 11:357-368.

McIntosh et al., 1989, "Traumatic Brain Injury in the Rat: Characterization of a Lateral Fluid-Percussion Model", *Neuroscience*, 28:233-244.

Smith and Kotwal, 2001, "Virokines: novel immunomodulatory agents", *Exp. Opin. Biol. Ther.*, 3:343-357.

Seet et al., 2003, "Poxviruses and Immune Evasion", *Annu. Rev. Immunol.*, 21:377-423.

Turner and Moyer, 2002, "Poxvirus immune modulators: functional insights from animal models", *Virus Research*, 88:35-53.

Buller and Palumbo, 1991, "Poxvirus Pathogenesis", *Microbiological Reviews*, 55:80-122.

Tanno et al., 1992, "Breakdown of the Blood-Brain Barrier after Fluid Percussive Brain Injury in the Rat. Part 1: Distribution and Time Course of Protein Extravasation", *J. Neurotrauma*, 9:21-32.

Kahn et al., 2003, "Dose-Dependent Inhibition of Complement in Baboons by Vaccinia Virus Complement Control Protein: Implications in Xenotransplantation", *Transplantation Proceedings*, 35:1606-1608.

Kotwal et al., 1998, "The inflammation modulatory protein (IMP) of cowpox virus drastically diminishes the tissue damage by down-regulating cellular infiltration resulting from complement activation", *Mol. Cell. Biochem.*, 185:39-46.

Anderson et al., 2003, "Vaccinia virus complement control protein inhibits hyperacute xenorejection in a guinea pig-to-rat heterotopic cervical cardiac xenograft model by blocking both xenoantibody binding and complement pathway activation", *Transplant Immunology*, 11:129-135.

Smith et al., 2000, "Conserved Surface-Exposed K/R-X-K/R Motifs and Net'Positive Charge on Poxvirus Complement Control Proteins Serve as Putative Heparin Binding Sites and Contribute to Inhibition of Molecular Interactions with Human Endothelial Cells: a Novel Mechanism for Evasion of Host Defense", *J. Virology*, 74:5659-5666.

* cited by examiner

THERAPEUTIC METHOD OF TREATING BRAIN TRAUMA IN RODENTS WITH VCP

PRIORITY OF INVENTION

This application claims priority from U.S. Provisional Application No. 60/306,671, filed 20 Jul. 2001.

BACKGROUND OF THE INVENTION

Traumatic brain injury (TBI) is a major public health concern, as it is a common result of automobile accidents, falls, and acts of violence. TBI can result in a prolonged loss of cognitive function that may involve several memory, learning, and motor skill deficits. This functional impairment can be attributed to both the initial physical impact and to secondary events that result from the intracranial inflammatory response, including activation of the complement (C) cascade.

Because inflammation is essential for repair and restoration of homeostatic, the challenge is to identify and regulate the components that are neurotoxic. It has been shown that C fragments are present and active within the injured cortex following a lateral fluid percussion (FP) brain injury in the rat. In addition, there is a significant increase in the number of neutrophils within this same region 24 h after trauma (Keeling et al., *J. Neuroimmunol.*, 105:20 (2000)).

C activation results in the formation of several pro-inflammatory mediators and potent leukocyte chemoattractants, including the anaphylatoxins C3a, C4a, and C5a, which propagate the cellular phase of the inflammatory response. Other downstream effector functions of C activation contribute to tissue destruction through formation of the lytic terminal membrane attack complex (MAC), neutrophil chemotaxis, free radical production, cytokine release, and increased vascular permeability (Bellander et al., *J. Neurosurg.*, 85:468 (1996); Frank et al., *Immunol. Today*, 12:322 (1991); and Kirschfink, *Immunopharmacology*, 38:51 (1997)).

The vaccinia virus complement control protein (VCP) was the first identified soluble microbial protein with C binding capabilities (Kotwal et al., *Science*, 250:827 (1990); and Kotwal et al., *Nature*, 335:176 (1988)). It is related both structurally and functionally to human C regulatory molecules, including soluble C receptor one (sCR1), C4b-binding protein (C4b-BP), Factor H (FH), membrane cofactor protein (MCP), and decay accelerating factor (DAF) (Murthy et al., *Cell*, 104:301 (2001)). The molecular mimicry of these mammalian proteins that VCP exhibits makes it an important molecule for evasion of host defense against viral infection (Kotwal, *J. Leukoc. Biol.*, 62:415 (1997); and Kotwal, *Immunol. Today*, 21:242 (2000)).

VCP binds C components C3 and C4, and acts as a cofactor for Factor I cleavage of C3b and C4b, thereby inhibiting downstream activation of both the classical and alternative C pathways (Kotwal et al., *Science*, 250:827 (1990); and McKenzie et al., *J. Infect. Dis.*, 166:1245 (1992)). It was also recently discovered that VCP can bind to heparin and heparan sulfate proteoglycans (Kotwal et al., *Mol. Cell Biochem.*, 185:39 (1998a); Murthy et al., *Cell*, 104:301 (2001); Reynolds et al., *Advances in Animal Virology*, S. Jameel and L. Villarreal (eds), Oxford & IBH Publishing Co., pgs. 343-348 (1999); and Smith et al., *J. Virol.*, 74:5659 (2000)), possibly endowing VCP with an additional anti-inflammatory function, the ability to inhibit cellular migration (Reynolds et al., *Advances in Animal Virology*, S. Jameel and L. Villarreal (eds), Oxford & IBH Publishing Co., pgs. 343-348 (1999)). It is possible that by binding to heparin and heparin-like molecules on the surface of the endothelial lining of blood vessels, VCP will be able to block the receptors for leukocyte chemotaxis. Therefore, VCP possess two distinct mechanisms of action, one that inhibits the C-mediated effects of inflammation, and one that may more directly inhibit cellular infiltration.

Currently, there is a need for methods for reducing the negative effects of brain trauma.

SUMMARY OF THE INVENTION

Applicant has discovered that VCP can improve cognitive function in rats following a FP brain injury. Injured animals that received VCP exhibited significant spatial memory recovery, as compared to controls, when tested in the Morris Water Maze. These experiments demonstrate that inhibition of C activation and/or inhibition of cellular infiltration in the injured brain can reduce the complications associated with brain injury.

Accordingly, the invention provides a method to treat a complication of neuronal injury in a mammal having a complement cascade comprising inhibiting the complement cascade.

The invention also provides a method to treat a complication of neuronal injury in a mammal comprising inhibiting cellular infiltration to a site of the neural injury.

The invention also provides a method to treat a complication of neuronal injury in a mammal having a complement cascade comprising administering an effective amount of an agent to the mammal to inhibit the complement cascade.

The invention also provides a method to treat a complication of neuronal injury in a mammal comprising administering an effective amount of an agent to the mammal to inhibit cellular infiltration to a site of the neural injury.

The invention also provides pharmaceutical composition comprising a pharmaceutically acceptable carrier and a therapeutically effective amount of a virus that expresses vaccinia virus complement control protein, smallpox inhibitor of complement, a human complement regulating protein, or C1q-binding peptide.

The invention also provides the use vaccinia virus complement control protein, smallpox inhibitor of complement, compstatin, a compstatin analog, a human complement regulating protein, complement C2 receptor inhibitor trispanning, a C1q-binding peptide, C1-inhibitor, a terpenoid, or an antibody for the manufacture of a medicament useful for reducing memory loss injury following neural injury in a mammal.

The invention provides VCP for use in medical therapy (e.g. reducing memory loss following neuronal injury), as well as the use of VCP for the manufacture of a medicament useful for the treatment of the negative effects of brain trauma.

The invention also provides a method of reducing neural damage (e.g. damage caused by traumatic brain injury or traumatic spinal cord injury) comprising the administration of complement control protein operatively linked to a vector (e.g. vaccinia virus or lentivirus).

The invention also provides a recombinant vector wherein the viral envelope protein of HIV has been substituted with G glycoprotein of the vesicular stomatitis virus (VSV-G)

The invention also provides a method to treat a complication of neuronal injury in a mammal comprising administering an effective amount of VCP to the mammal.

DETAILED DESCRIPTION

Figure 1:
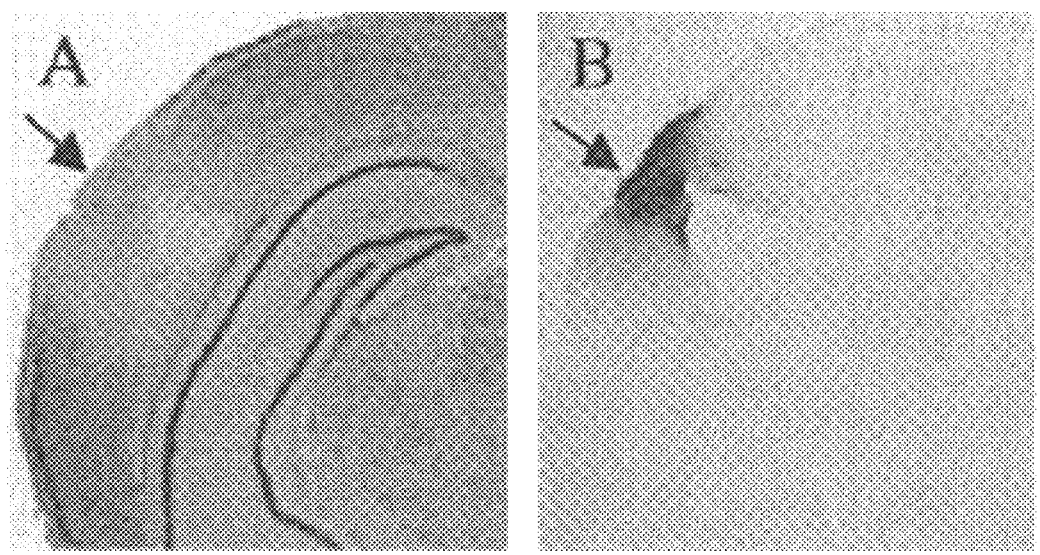
FIG. 1. Intraparenchymal injections of b-VCP are localized within the injury site following FP injury. Rats were injected with b-VCP 15 minutes after FP (a and b, 10 µl into the injured cerebral cortex) and euthanized 24 h later. Sections stained with cresyl violet demonstrate typical pattern of cell death after FP injury (a, arrow). Injections of b-VCP are localized within the primary site of cell damage (b, arrow) after FP injury. Cell loss was not evident in sham-injured animals following administration of b-VCP, although the Hamilton syringe caused minor trauma. Error bars indicate s.e.m.

As used herein "memory loss" includes both the loss of memory as well as a diminution in the ability to retain facts.

The term "neural injury" includes physical trauma to the brain or spinal cord, as well as trauma that results from disease or infection.

The neurological complications of traumatic brain injury (TBI) include an increased risk of developing Alzheimer's disease. Activation of the complement system during the post-acute stages of TBI may lead to a self-perpetuating cycle of chronic inflammation and neurodegeneration. Ultimately, impairments in memory and learning may result from the chronic inflammation and neuropathology. It is predicted that early intervention after TBI, by inhibition of the complement cascade and/or by inhibition of cell infiltration, may prevent or ameliorate the memory loss, learning impairment, or the development of symptoms of Alzheimer's disease.

The term treat includes preventing a complication from arising, slowing the development of a complication, ameliorating the severity of the complication, as well as eliminating the complication completely.

In one embodiment, the methods of the invention can be carried out by administering a therapeutic agent to produce the described therapeutic effect. Representative therapeutic agents that can be administered according to the methods of the invention include agents that inhibit one or more components of the complement cascade, or that inhibit the activity of a complement receptor. For example, such agents include vaccinia virus complement control protein, smallpox inhibitor of complement, compstatin, a compstatin analog, a human complement regulating protein, complement C2 receptor inhibitor trispanning, a C1q-binding peptide, C1-inhibitor, a terpenoid, an antibody, and a complement receptor antagonist (e.g. AcPhe[Orn-Pro-D.Cyclohexylalanine-Trp-Arg](AcF-[OPdChaWR]).

Representative agents and methods for their preparation are described by, Inal and Schifferli, *J. Immunol.*, 168:5213-5221 (2002); Kirschfink, *Immunol. Rev.*, 180:177-189 (2001); Strachan et al., *Br. J. Pharmacol.*, 134:1778-1786 (2001); Horstick et al., *Circulation*, 104:3125-3131 (2001); Roos et al., *J. Immunol.*, 167:7052-7059 (2001); Monsinjon et al., *Fundam. Clin. Pharmacol.*, 15:293-306 (2001); Nagahama et al., *Transpl. Int.*, 15:205-211 (2002); and Furlong et al., *Immuopharmacology*, 48:199-212 (2000)

The methods of the invention can also be carried out by administering a recombinant vector, such as, for example, a plasmid, phagemid, cosmid, virus, recombinant virus (e.g. a recombinant virus that expresses vaccinia virus complement control protein, smallpox inhibitor of complement, or an antisense message to a component acting in the complement cascade).

As used herein a complement inhibitor is an agent that inhibits one or more components of the complement cascade.

In cases where agents are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The therapeutic agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present agents may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active agent may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of active agent in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active agent, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active agent may be incorporated into sustained-release preparations and devices.

The active agent may also be administered intravenously or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the agents can be determined by comparing their in vitro activity, and in vivo activity in animal models. Methods for the extrapolation of effective dosages in mice, and other animals, to humans are known to the art; for example, see U.S. Pat. No. 4,938,949.

The amount of the agent, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of an agent to inhibit the complement cascade or to inhibit cellular infiltration can be determined using pharmacological models which are well known to the art. For example, see The Merck Manual, 17th ed., Merck Research Laboratories, Whitehouse Station N.J., USA, 1999, page 1022; Kotwal et al., *Science*, 250:827 (1990); and Rosengard et el., *P.N.A.S.* (USA) 2002, 99, 8808-8813.

The invention will now be illustrated by the following non-limiting Examples.

EXAMPLE 1

Materials and Methods

Lateral Fluid Percussion Brain Injury

Male Sprague-Dawley rats (325-375 g) were anesthetized with sodium pentobarbital (60 mg/kg, i.p.) 10 min after receiving 0.15 ml of atropine (0.4 mg/ml, i.m.), placed into a stereotaxic frame, and surgical procedures were performed as previously described (McIntosh et al., *Neuroscience*, 28:233 (1989)). A Luer-loc hub was attached to a 5 mm diameter craniotomy, which was centered 3 mm lateral to the sagittal suture and 4.5 mm posterior to bregma. The rats (n=22) were removed from the stereotaxic frame, attached to a lateral fluid percussion brain injury (FP) device (Scientific Instruments, University of Washington, Seattle, Wash.) and subjected to a brain injury of moderate severity (4.5 atm). Additional sham control animals (ntl 1) underwent anesthesia and surgery but did not receive an injury. All experiments were performed in compliance with the relevant laws and guidelines for animal use set forth by the University of Washington.

Production of and Purification of VCP VCP was produced by two different methods, one involving a natural infection of RK-13 cells with vaccinia virus (Kotwal et al., *Science*, 250: 827 (1990); and Kotwal et al., *Mol. Cell Biochem.*, 185:39 (1998a)), and the other from recombinant techniques (Murthy et al., *Cell*, 104:301 (2001); Smith et al., *J. Virol.*, 74:5659 (2000)), as previously described. After the purification steps, the functional activity of VCP was confirmed by its ability to inhibit complement-mediated lysis of sheep erythrocytes in a previously described hemolysis microassay (Kotwal et al., *Science*, 250:827 (1990)).

Biotinylation of VCP

1700 Units of lyophilized VCP (1 Unit of activity=the amount of VCP needed to inhibit 50% of complement-mediated hemolysis of sheep erythrocytes) were reconstituted in 2 ml PBS and the pH was adjusted to 9.0 using 0.5 M sodium bicarbonate buffer. Next, 50 mg of N-hydroxysuccininide-biotin (Sigma, St. Louis, Mo.) was dissolved in 1 ml of N,N-dimethyl formamide. The two were added together at a ratio of 200 µl biotin: 2 ml VCP and incubated in the dark for 3 h at room temperature. The reaction was stopped by adding 220 µl of 1 M NH$_4$Cl for a final concentration of 0.1 M. Next, the mixture was transferred to a centrifugal concentrator and washed 3 times with PBS at 5000 rpm to remove any unbound biotin. The final volume was approximately 60 µl of biotinylated VCP.

Administration of VCP

To optimize delivery methods for the VCP, animals received injections of biotinylated VCP (b-VCP) into the brain 15 minutes after FP (n=5) or sham injury (n=3). The b-VCP (500 units diluted in 5 or 10 μl of sterile saline) was injected using a Hamilton syringe into either the left lateral ventricle (stereotaxic coordinates from bregma: −3.8 mm antero-postero, −5.2 mm dorso-ventro and 5.0 mm lateral), the center of the injury site within the brain parenchyma (coordinates from bregma: −5.2 mm antero-postero, −1.7 mm dorso-ventro and 6.0 mm lateral), or the subcortical white matter within the primary injury site (coordinates from bregma: −4.8 mm antero-postero, −2.6 mm dorso-ventro and 5.6 mm lateral). Anesthetized animals were perfused 24 h later with saline followed by 4% paraformaldehyde. The brains were removed, post-fixed with paraformaldehyde overnight, and then transferred into a solution of 25% sucrose in PBS. To investigate the effects of VCP on behavior, animals were divided into 4 groups: FP+VCP (n=8), FP+saline (n=9), sham+VCP (n=3), sham+saline (n5). The VCP (500 units in 10 μl saline, or 2.25 μg/ml) and saline (100) were injected into the brain parenchyma as described above.

Immunocytochemistry

Coronal brain sections were cut throughout the extent of the injury (−1.8 to −6.5 mm posterior to bregma) into 40 μm thick sections on a microtome. The tissue sections were processed as follows: incubation in 1% hydrogen peroxide in tris-buffered saline (TBS) for 10 minutes, incubation in a 1:100 dilution of avidin-biotin-peroxidase complex (Vector Laboratories, Burlingame, Calif.), and incubation in 0.05% solution of 3,3-diaminobenzidine and 0.01% hydrogen peroxide for 10 minutes. The sections were then mounted onto slides. Cresyl violet was used to stain alternate sections.

Cognitive Testing

Using a modified 2-day Morris Water Maze procedure (Hicks et al., *Res. Neurol. Neurosci.*, 12:41 (1998)). the animals were trained to find a hidden platform in a pool. Training began 13 days after FP or sham injury, and consisted of performing two blocks of four acquisition trials per day for 2 days, for a total of 16 trials. A blinded observer recorded the time required for each animal to find the platform (goal latency) in each trial and calculated the means for each trial block. After completing the last acquisition trial, animals underwent a single probe test to assess their spatial memory. The platform was removed and the swim pattern of each animal was videotaped for 30 seconds. A video motion analyzer (Videomex V, Columbus Instruments, Columbus, Ohio) computed the mean distance of the swim path from the previous platform location (proximity), and the percent of time spent in the quadrant of the pool where the platform was previously located (quadrant time). The data were analyzed with a one-way ANOVA and Pisher post-test comparison using the SYSTAT (version 9.0) program.

Results

Given the difficulties of targeting therapeutic agents to the injured rat brain, the C inhibitor VCP was labeled with biotin prior to administration in order to determine which injection site could most effectively distribute the protein. Animals were injected with 5-10 μl (500 units) of biotinylated VCP (b-VCP) into the brain parenchyma or lateral ventricle 15 minutes after receiving a FP or sham injury (n=8), and were euthanized 24 h later. Histological staining of coronal sections of the parieto-occipital cortex showed that the 10 μl injections of b-VCP into the parenchyma were most effective at targeting the region of the cortex where cells are typically damaged following a FP injury of this level of severity (FIGS. 1a and b). In addition, injections of VCP into the cortex of sham-injured rats did not result in cell damage (FIGS. 1c and d). These results demonstrate that administration of VCP into the parenchyma: targets injured regions of the brain following FP injury, is present until at least 24 h after injection, and does not induce overt cell damage in control animals.

Figure 2:
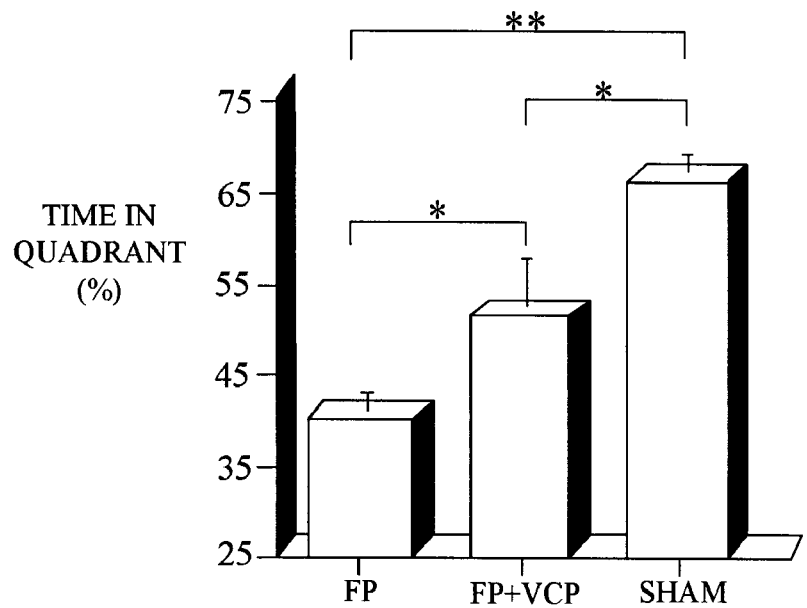
FIG. 2. Spatial learning is impaired after FP injury and not improved with VCP. Rats were injected with VCP or saline 15 minutes after FP or sham injury. Two weeks later, the rats were trained to find a hidden platform in a MWM by using visual cues. As compared to the controls, the injured rats showed a delayed and impaired ability to complete the task (*, $P<0.05$; , $P<0.005$; *, $P<0.001$). Injection of VCP after FP injury did not attenuate the impairment in spatial learning. However, all groups demonstrated some improvements in goal latencies improved between the first and last trial blocks ($P<0.001$). Error bars indicate s.e.m.

Since cognitive deficits are one of the hallmarks of traumatic brain injury, the effects of VCP on learning and memory in rats were evaluated following FP injury. Fifteen minutes after the animals received a FP injury or a sham injury, VCP or saline was injected into the cerebral cortex. Two weeks later, the animals were tested in the Morris Water Maze, which is one of the most commonly used behavioral measures for evaluating cognitive impairments associated with FP injury (Hamm, *J. Neurotrauma*, 13:317 (1996); Hicks et al., *Res. Neurol. Neurosci.*, 12:41 (1998); Leoni et al., *Exp. Neurol.*, 166:442 (2000); and Smith et al., *J. Neurotrauma*, 8:259 (1991)). Data analysis was begun by comparing the performance of VCP-treated and untreated control rats, and upon finding no differences between groups, the sham-injured animals were collapsed into one group. Goal latencies were then compared across injured and sham rats. In the first trial block, goal latencies were similar across groups (FIG. 2). By the second trial block, sham animals located the platform more quickly than injured rats. Indeed, control animals demonstrated full acquisition for learning the task by the second trial block and did not show further improvements with additional training. The injured rats continued to improve on the task over the four trial blocks, however they did not reach the performance levels of the control animals. The longer latencies in the FP groups could not be explained by differences in swim speeds, and were not attenuated by administration of VCP (FIG. 2). These results demonstrate that all of the animals were capable of spatial learning, but that the FP-injured animals did not perform as well as the controls, which is consistent with previous studies (Blaha et al., *Neuroscience*, 99:483 (2000); and Pike et al., *Pharmacol. Biochem. Behav.*, 57:785 (1997).

Figure 3:
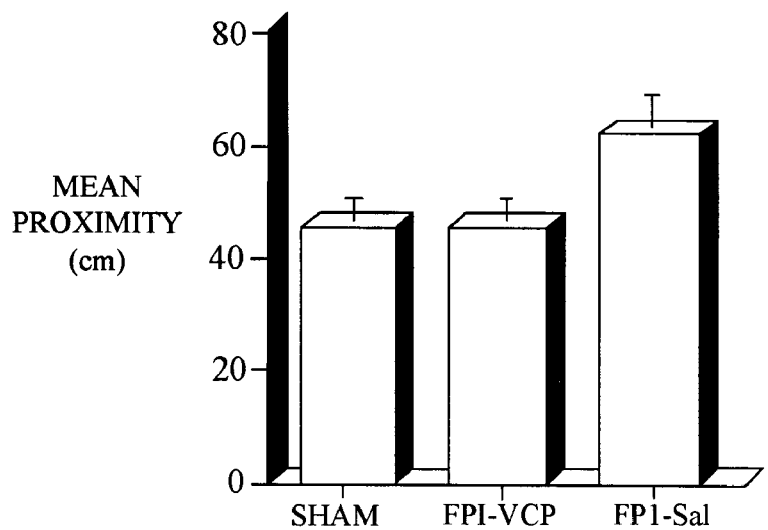
FIG. 3. VCP attenuates impairments in spatial memory following FP. After completing the last acquisition trial, rats underwent a probe test in the MWM. The mean distance of the swim path (proximity) in the FP group was farther from the previous platform location than in sham or FP+VCP groups (a). Similarly, the percent time spent in the quadrant previously containing the platform was shorter in the FP group than sham or FP+VCP groups (b). (*, $P<0.03$; , $P<0.01$; *, $P<0.002$).

After completing the last acquisition trial, animals underwent a single probe test to assess their spatial memory. The platform was removed and the swim pattern of each animal was videotaped for 30 seconds. The mean distance of the swim path from the previous platform location for the injured animals that received VCP injections was not only shorter than that of untreated FP animals, but also approached normal values (FIG. 3a). Furthermore, injured animals that received VCP spent a greater percentage of time in the quadrant of the pool where the platform was previously located than injured, untreated animals (FIG. 3b).

Discussion

As early as two hours after FP injury, activation fragments of the third component of the complement system (C3) begin accumulating in the injured cortex in a time-dependent manner (Keeling et al., *J. Neuroimmunol.*, 105:20 (2000)). By 24 h, increases not only in C3 activation, but also in the common terminal lytic portion of the complement (C) cascade, the membrane attack complex (MAC). Upregulation of C within the injured brain, either by serum leakage through a dysfunctional BBB or by intracerebral synthesis, produces proinflammatory mediators such as C3a and C5a that enhance leukocyte extravasation, cytokine expression, microglia and astrocyte activation, scar formation, and neuronal death (Keeling et al., *J. Neuroimmunol.*, 105:20 (2000); Morgan et al., *Immunol. Today*, 17:461 (1996); and Stahel et al., *Brain Res. Brain Res. Rev.*, 27:243 (1998)). Our findings suggest that FP injury results in a local inflammatory response that includes a fully activated C system, which may contribute to neuronal lysis and associated cognitive deficits. Indeed, these C fragments accumulated in the same regions of the injured cortex and underlying hippocampus where previous studies have shown increases in neuronal loss (Hicks et al., *Acta Neuropathol.*, 91:236 (1996); and McIntosh et al., *Neuroscience*, 28:233 (1989)), neutrophil accumulation, and loss of blood brain barrier (BBB) integrity (Soares et al., *J. Neurosci.*, 15:8223 (1995); and Tanno et al., *J. Neurotrauma*, 9:21 (1992)). Another study showed that administration of the human C inhibitor, sCR1, just prior to injury reduces neutrophil accumulation in the brain after a weight drop trauma (Kaczorowski et al., *J. Cereb. Blood Flow Metab.*, 15:860 (1995)), suggesting an important role for C in the cellular influx that ensues after injury.

The success of the Poxvirus family of DNA viruses is due, in no small part, to its collective ability to encode proteins that subvert the host immune system. VCP, the major secretory protein of vaccinia virus, is one such molecule, as it is related both structurally and functionally to human C regulatory molecules (Kotwal et al., *Science*, 250:827 (1990); and Kotwal et al., *Nature*, 335:176 (1988)). Although VCP is structurally similar to human C4b-binding protein (hC4b-BP) and functionally similar to sCR1, it is much smaller, consisting of only four of the short consensus repeats (SCRs) that are found in all C regulatory proteins. In comparison, sCR1 consists of approximately 30 SCRs, while hC4b-BP is a giant multimeric molecule comprised of 60 SCRs. Early studies using VCP showed that through its ability to bind C3 and C4, VCP could prevent antibody-mediated virus neutralization, allowing the virus to evade destruction by the host immune response (Isaacs et al., *Proc. Natl. Acad. Sci. USA*, 89:628 (1992)). By blocking C at the early stages, VCP also prohibits formation of the proinflammatory chemotactic factors C3a, C4a, and C5a, and thus, reduces cellular infiltration. Two mouse models of poxvirus infection have demonstrated that VCP can modulate C-mediated inflammation and subsequent tissue damage in vivo. Studies using BALB/c mice injected in the footpad with wildtype cowpox virus (CPV) or a mutant that lacked the VCP homologue, called inflammation modulatory protein (IMP), showed that the absence of IMP significantly increased the swelling response and infiltration of inflammatory cells in the footpads (Miller et al., 1997). Similar results were found when these injections were performed in a mouse connective tissue airpouch model (Kotwal et al., *Mol. Cell Biochem.*, 185:39 (1998a)).

Unlike many other C regulatory proteins, VCP also has the ability to bind heparin and heparan sulfate proteoglycans (Kotwal et al., *Mol. Cell Biochem.*, 185:39 (1998a); Murthy et al., *Cell*, 104:301 (2001); Reynolds et al., *Advances in Animal Virology*, S. Jameel and L. Villarreal (eds), Oxford & IBH Publishing Co., pgs. 343-348 (1999); and Smith et al., *J. Virol.*, 74:5659 (2000)). This property endows VCP with various novel functions, including the ability to reduce the chemotactic migration of leukocytes in vitro in response to the chemokine monocyte inflammatory protein 1α (MIP-1α) (Reynolds et al., *Advances in Animal Virology*, S. Jameel and L. Villarreal (eds), Oxford & IBH Publishing Co., pgs. 343-348 (1999)). In addition, VCP has the ability to bind heparin granules in mast cells after uptake, possibly allowing for prolonged tissue retention. Through its interaction with heparin sulfate proteoglycans, VCP can also inhibit the binding of antibody to MHC class I molecules on the surface of human endothelial cells, and prevent the interaction of neutrophils and natural killer cells with pig aortic endothelial cells (PAECS), thus inhibiting cell death (Al-Mohanna et al., *Transplantation*, In Press (2001)).

Because of its compact size and ability to bind both C and heparin, VCP has strong therapeutic potential for many different C-mediated inflammatory processes, including brain and spinal cord injury, Alzheimer's disease (Daly et al., *Neurobiol. Aging*, 19:619 (1998)), multiple sclerosis, autoimmune disorders, and xenograft rejection (Al-Mohanna et al., *Transplantation, In Press* (2001)).

It is possible that a dual effect of both C and heparin binding, rather than C inhibition alone, is responsible for the improved spatial memory in the above example. Whichever the case, the results demonstrate that VCP has the ability to alleviate memory impairment, one of the most prevalent, devastating, and enduring effects of brain injury (Levin et al., *J. Neurosurg.*, 66:234 (1987)).

An important issue that may need resolution is how best to deliver bioactive VCP. It may not always be practical to deliver VCP directly to the site of injury, unless the patient requires surgical intervention. The recent determination of the 3-D structure of VCP (Murthy et al., Cell, 104:301 (2001)) will aid in the design of novel synthetic compounds that can inhibit complement and easily traverse the blood brain barrier.

Figure 4:
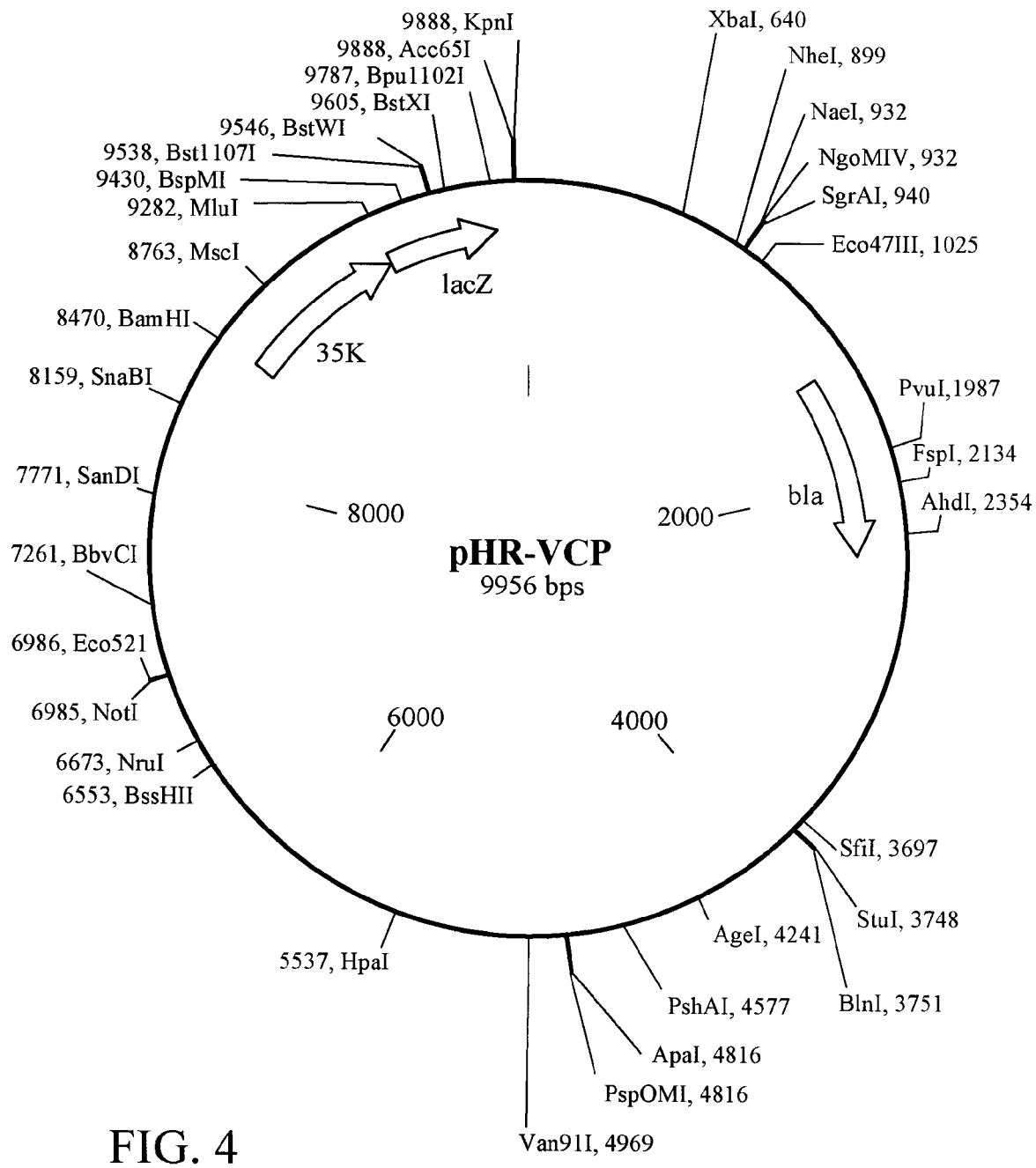
FIG. 4. illustrates the construction of a lentivirus-VCP gene delivery vehicle.

In addition to the vaccinia virus vector, lentiviruses may be constructed to be operatively linked to VCP. FIG. 4 shows a diagram of the construction of a lentivirus-VCP gene delivery vehicle. Lentiviral vectors are an excellent mode of transferring DNA into neural cells because, unlike other retroviral vectors, lentiviruses, which are based on the human immunodeficiency virus (HIV), can infect terminally differentiated cells. Applicants have developed a system that requires only an engineered cell line that is transformed with a plasmid containing the DNA of interest. The viral envelope protein of HIV has been substituted with G glycoprotein of the vesicular stomatitis virus (VSV-G) which expands its infectivity to a broad range of host cells and species. Accordingly, the invention also provides a recombinant vector wherein the viral envelope protein of HIV has been substituted with G glycoprotein of the vesicular stomatitis virus (VSV-G). This vector has an expanded host range relative to the original lentivirus.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for ameliorating the diminished ability to retain new facts in a rodent following a percussion neuronal injury comprising administering to the rodent an effective amount of VCP and a pharmaceutically-acceptable carrier, wherein the VCP is administered directly to the site of neuronal injury within about 15 minutes of the neuronal injury, wherein the effective amount of the VCP ameliorates the diminished ability to retain new facts in the rodent following the neuronal injury.

2. A method for ameliorating the diminished ability to retain new facts in a rodent following a percussion neuronal injury comprising administering to the rodent an effective amount of VCP and a pharmaceutically-acceptable carrier intravenously within about 15 minutes of the neuronal injury, wherein the rodent has a compromised blood brain barrier resulting from said percussion neuronal injury, wherein the effective amount of the VCP ameliorates the diminished ability to retain new facts in the rodent following the neuronal injury.

* * * * *